United States Patent [19]
Klinger et al.

[11] Patent Number: 5,561,881
[45] Date of Patent: Oct. 8, 1996

[54] ELECTRIC TOOTHBRUSH

[75] Inventors: Thomas Klinger, Villach; Maximilian Pachel, Maria Saal; Martin Sonnek; Erich Krammer, both of Klagenfurt, all of Austria

[73] Assignee: U.S. Philips Corporation, New York, N.Y.

[21] Appl. No.: 409,123

[22] Filed: Mar. 22, 1995

Related U.S. Application Data

[63] Continuation of Ser. No. 216,572, Mar. 22, 1994, abandoned.

[51] Int. Cl.⁶ ......................................... A46B 13/02
[52] U.S. Cl. ........................... 15/22.1; 15/105; 15/167.1; 433/216
[58] Field of Search ............................ 15/22.1, 22.2, 15/22.4, 23, 24, 167.1, 105; 433/216

[56] References Cited

U.S. PATENT DOCUMENTS

| | | | |
|---|---|---|---|
| 4,450,599 | 5/1984 | Scheller et al. | 15/22.1 |
| 4,698,869 | 10/1987 | Mierau et al. | 15/22.1 |

FOREIGN PATENT DOCUMENTS

| | | | |
|---|---|---|---|
| 4012413 | 10/1991 | Germany | 15/22.1 |
| 5237014 | 9/1993 | Japan | 15/22.1 |

Primary Examiner—Gary K. Graham
Attorney, Agent, or Firm—Ernestine C. Bartlett

[57] ABSTRACT

An electric toothbrush comprising a toothbrush device (100) and a charge device (200) is operative to provide an accurate determination and an adequate indication of the duty performance of toothbrushing. The toothbrush device (100) comprises a supply unit (110), a control unit (120) and a driving portion (130). The control unit (120) is provided with a time-measuring portion (121) for measuring the duty time during toothbrushing, a pressure-measuring portion (122) for measuring the duty pressure during toothbrushing, a position-determining portion (124) for determining the duty position during toothbrushing and a computing portion (123) to compute a duty performance. An accurate determination of the duty performance is achieved in computing portion (123) which computes the duty performance in response of the duty time, the duty pressure and the duty position. "duty" time, pressure and position being the time, pressure and position during operation of the toothbrush during toothbrushing. The duty performance and optionally the duty time, duty pressure and duty position are indicated by indication portion (2 10) located either on the toothbrush device (100) or on the charge device (200). In case of a detachable toothbrush device (100), the control unit (120) in the toothbrush device (100) and the indication portion (210) in the charge device (200) may communicate via a wireless communication link.

32 Claims, 3 Drawing Sheets

5,561,881

ELECTRIC TOOTHBRUSH

This is a continuation of application Ser. No. 08/216,572, filed Mar. 22, 1994, now abandoned.

FIELD OF THE INVENTION

The present invention relates to an electric toothbrush comprising a control unit comprising a time-measuring means for measuring the duty time i.e. the duration of a period of operation of the apparatus during toothbrushing and a pressure-measuring means for measuring the duty pressure i.e. the pressure as a result of operation of the appartus during toothbrushing, a driving means, which is electrically coupled to the control unit, the driving means comprising an electro-mechanical means for driving a brush, and an indication means, which is driven by the control unit for informing a user of the electric toothbrush. The word "duty" as used herein means operation of the apparatus during toothbrushing.

An aforesaid toothbrush can be used to clean the teeth of a human being to protect the teeth from caries and gingivitis (tooth decay).

BACKGROUND OF THE INVENTION

An aforesaid toothbrush is known inter alia from U.S. Pat. No. 4,450,599. In that Patent the main cause of caries and gingivitis is acknowledged to be a lasting formation of dental plaque and an adequate removal of dental plaque is mentioned to be the desired performance of toothbrushing. In order to achieve an adequate removal of dental plaque a duty time above a minimum time and a duty pressure between a minimum and a maximum pressure are acknowledged to be desired. As a consequence the control means of the known toothbrush is provided with the time-measuring means and the pressure-measuring means to determine the duty time and the duty pressure as well as to drive the indication means to inform the user of the duty performance, i.e. the achieved removal of dental plaque. In the known toothbrush, to determine the minimum time and the desired pressure, the time-measuring means is only activated, when the pressure-measuring means determines a duty pressure between the minimum and the maximum pressure, and the indication means is only activated, when the time measuring-means determines a duty time exceeding the minimum time. However, notwithstanding the design and the construction of the known toothbrush, the achieved removal of dental plaque, when the indication means is activated, and the disclosed display of the duty performance are found to be inaccurate.

As a consequence, the present invention has the object to provide an electric toothbrush, which provides an accurate determination and an adequate indication of the duty performance.

SUMMARY OF THE INVENTION

An electric toothbrush in accordance with the invention is characterized in that the control unit further comprises a computing means for computing a duty performance from the duty time and the duty pressure, the time-measuring means and the pressure-measuring means driving the computing means and the computing means driving the indication means, and in that the indication means is operative to inform the user of the duty performance during or after toothbrushing. The invention is based on the view that the electric toothbrush, to provide the accurate determination and the adequate indication, must comprise an intelligent unit (the computing means) to compute the duty performance from the leading parameters of toothbrushing and must serve a suited possibility to inform the user in a proper way. Whereas the leading parameters are meant to be the parameters that have a direct influence on the performance of toothbrushing, the computing means are meant to be an electrical circuit that continuously computes the actual performance from the leading parameters. In addition to the duty time and the duty pressure a further parameter will be disclosed in the following description. Moreover, several possibilities to implement the indication means will be described. Nevertheless, the computing unit enables the desired determination and indication.

A further embodiment of an electric toothbrush in accordance with the invention is characterized in that the duty performance is the product of a scale factor, the duty time and the duty pressure. As life duty performance depends inter alia on the duty time and the duty pressure, the product of the duty time and the duty pressure is found to be an accurate indication of the achieved performance during toothbrushing. However, since a soft pressure is insufficient and a strong pressure is undesirable for a satisfactory performance, the influence of the duty pressure on the product may be reduced by a scale factor that is a function of the duty pressure. For instance, a low pressure may stretch and a high pressure may compress the time scale for reaching the duty performance. Further, the scale factor may be a function of both the duty time and the duty pressure.

A further embodiment of an electric toothbrush in accordance with the invention is characterized in that the control unit further comprises a position-determining means to determine the duty position during toothbrushing, the position-determining means driving the computing means and the computing means driving the indication means, and in that the computing means is operative to compute the duty performance from the duty position. The electric toothbrush comprising the position-determining means can be used to inform the user in an improved way, because the position-determining means is constructed to determine if the brush has cleaned only a part of the teeth. With reference to the drawings the position-determining means is further discussed herein below.

A further embodiment of an electric toothbrush in accordance with the invention is characterized in that the duty performance is an operation of the duty time, the duty pressure and the duty position. Although a simple determination of the duty performance may be based on the duty position only, a more accurate determination is achieved, when the duty performance is computed from the duty time, the duty pressure and the duty position. When computing the duty performance, the aforementioned product of the scale factor, the duty time and the duty pressure can be used.

A further embodiment of an electric toothbrush in accordance with the invention is characterized in that the control unit is adaptable to monitor a current, which is carried by the electro-mechanical means, the time-measuring means being operative to register the duty time in response to the difference of the present current and the idle current. When the duty time is measured from the current, which is carried by or supplied to the electro-mechanical means, the idle current of the electro-mechanical means must be detracted to achieve a proper indication of the present current and the duty time.

A further embodiment of an electric toothbrush in accordance with the invention is characterized in that the control unit is adaptable to monitor a current, which is carried by the electro-mechanical means, the pressure-measuring means being operative to register the duty pressure in response to the difference of the present current and the idle current. When the duty pressure is measured from the current, which is carried by or supplied to the electro-mechanical means, the idle current of the electro-mechanical means must be detracted to achieve a proportional relation of the present current and the duty pressure.

A further embodiment of an electric toothbrush in accordance with the invention is characterized in that the control unit is operative to measure and register the idle current, a returning dip in the characteristic of the current being recognised as the idle current. The electro-mechanical means needs an idle current, which is subject to a change during life-time. As a consequence, in order to achieve an accurate determination of the duty performance the idle current must be monitored and adapted permanently. Since the brush of the electric toothbrush is sometimes removed from the teeth during toothbrushing, the returning dip in the characteristic of the current can be considered as the idle current.

A further embodiment of an electric toothbrush in accordance with the invention is characterized in that the indication means comprise a display for indicating the duty performance. When an accurate determination of the duty performance is achieved, a satisfactory indication of the achieved performance is desired. As a consequence, the electric toothbrush in accordance with the invention is provided with the display, which indicates the duty performance during or after toothbrushing.

A further embodiment of an electric toothbrush in accordance with the invention is characterized in that the indication means comprise a display for indicating the duty time. Since the duty time is displayed, the user is informed of the effective time of toothbrushing. A reference to a minimum time in the display may inform the user of the performance in respect of the effective time.

A further embodiment of an electric toothbrush in accordance with the invention is characterized in that the indication means comprise a display for indicating the duty pressure. As a result of the display the user may adapt the expressed pressure when toothbrushing.

A further embodiment of and electric toothbrush in accordance with the invention is characterized in that the duty pressure is displayed as a segmental interval. The display of the duty pressure as a segmental interval informs the user of the softest and strongest pressure. A reference to a minimum and a maximum pressure in the display may inform the user of the performance in respect of the expressed pressure.

A further embodiment of an electric toothbrush in accordance with the invention is characterized in that the indication means comprise a display for indicating the duty position. As a result of the display the user may adapt the positions of the electric toothbrush.

A further embodiment of an electric toothbrush in accordance with the invention is characterized in that the indication means have a continuous display during toothbrushing. By the continuous display the duty performance during toothbrushing can be corrected and improved directly. In regard to the duty pressure and the duty position the continuous display is particular advantageous.

A further embodiment of an electric toothbrush in accordance with the invention is characterized in that the indication means have a temporary display after or before toothbrushing. The temporary display can inform the user for a short period before or after toothbrushing, the short period being able to start when the electric toothbrush is picked up or switched off.

A further embodiment of an electric toothbrush in accordance with the invention is characterized in that the electric toothbrush further comprises a charge device, the charge device comprising a charge unit to charge a rechargeable battery in a supply unit, the supply unit being coupled electrically to the control unit. The supply unit may comprise a rechargeable battery, which battery implies the need of the charge unit.

A further embodiment of an electric toothbrush in accordance with the invention is characterized in that the indication means comprise a display for indicating a status of the supply unit. The supply unit of the toothbrush in accordance with the invention may be provided with an ordinary battery, a rechargeable battery or a mains supply. In case of the ordinary and rechargeable battery the user is helped by the display of the actual condition of the battery.

A further embodiment of an electric toothbrush in accordance with the invention is characterized in that the indication means is located in the charge device, the control unit and the charge device being coupled by means of a wireless communication link. Since the electric toothbrush is held in a hand during toothbrushing, the continuous display can not be read by the user. The duty performance, however, can be corrected and improved the best during toothbrushing. As a consequence, the electric toothbrush in accordance with the invention is provided with the wireless control. The indication means located on the charge device can now be seen by the user.

A further embodiment of an electric toothbrush in accordance with the invention is characterized in that the wireless communication link comprises an infra-red transmitter located at the control unit and an infra-red receiver located at the charge device, the wireless communication being achieved by an infra-red transmission. Although the wireless communication can be implemented in several ways, the infra-red transmission is found to give an satisfactory result.

BRIEF DESCRIPTION OF THE DRAWINGS

The above aspects of the invention, and other (more detailed) aspects of the invention are further described and elaborated with reference to the accompanying drawing, in which.

In the figures corresponding parts are indicated by the same reference signs.

DETAILED DESCRIPTION OF THE PREFERRED EMBODIMENTS

Figure 1:
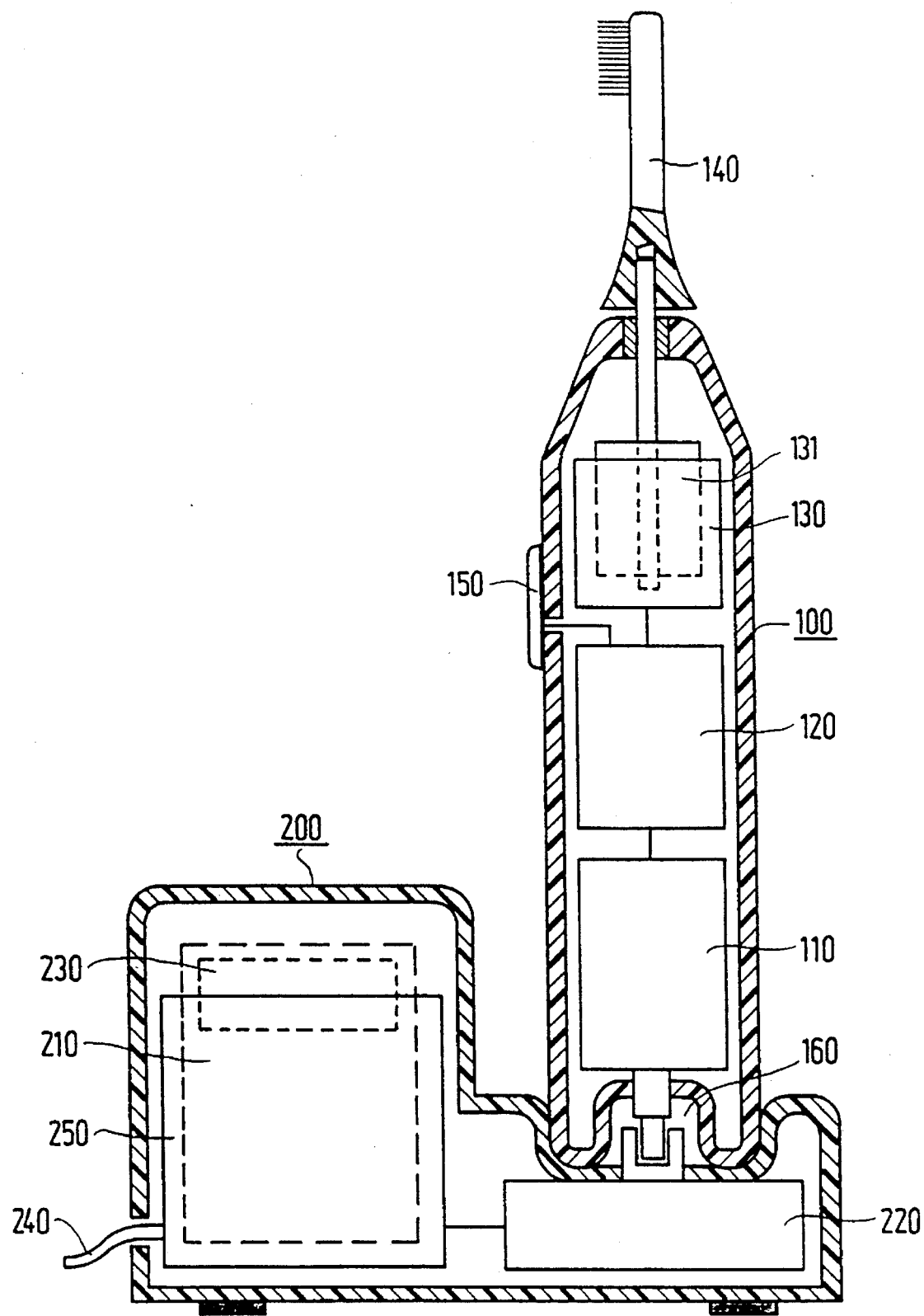
FIG. 1 shows an embodiment of an electric toothbrush in accordance with the invention.

In FIG. 1 an embodiment of an electric toothbrush in accordance with the invention is shown. The toothbrush incorporates an executive device (or toothbrush portion)100 and a charge device 200, which devices are both shown in a schematically way. The executive device 100 comprises a supply unit 110, a control unit 120, a driving means 130, a brush 140, and a switch 150. The supply unit is electrically coupled to the control unit 120 and (via the control unit 120) to the driving means 130 to provide a supply voltage. The control unit 120 is further coupled to the driving means 130 and the switch 150 to control the driving means 130, which means comprises an electro-mechanical means 131 to drive the brush 140. The charge device 200 comprises an indication means 210, a charge unit 220, an infra-red receiver 230, a power cord 240, and a voltage transformer 250. The indication means 210 is electrically coupled to the charge unit 220 for receiving a supply voltage and is coupled via the infra-red receiver 230 to receive data signals from the control means 120 in the executive device 100. The charge unit 220 receives supply voltage via the power cord 240 and the voltage transformer 250. In the embodiment shown, the charge device 200 comprises the charge unit 220 and the supply unit 110 is provided with a rechargeable battery. The executive device 100 and the charge device 200 are detachable and provided with a two-part connector 160, having a male part located on the supply unit 110 and a female part located on the charge unit 220. Another option is a two part transformer 250, having a primary winding in the charge device 200 and a secondary winding in the detachable executive device 100. Alternative configurations without detachable parts are also possible, in which case the supply unit 110 may comprise an ordinary battery or a mains adapter and the indication means may be located on the executive device 100. The supply means (110, 220, 240, 250) are not discussed further, since the individual components may be constructed conventionally as known from the prior art. Accordingly, the electro-mechanical means 131 as incorporated in the electric toothbrush is not discussed further; as known from the prior art, the electro-mechanical means 131 may move the brush in a longitudinal and/or rotary direction. The further functions of the electric toothbrush in accordance with the invention are discussed with reference to the Figures, which Figures show an example of the control unit 120 and an example of the indication means 210, respectively.

Figure 2:
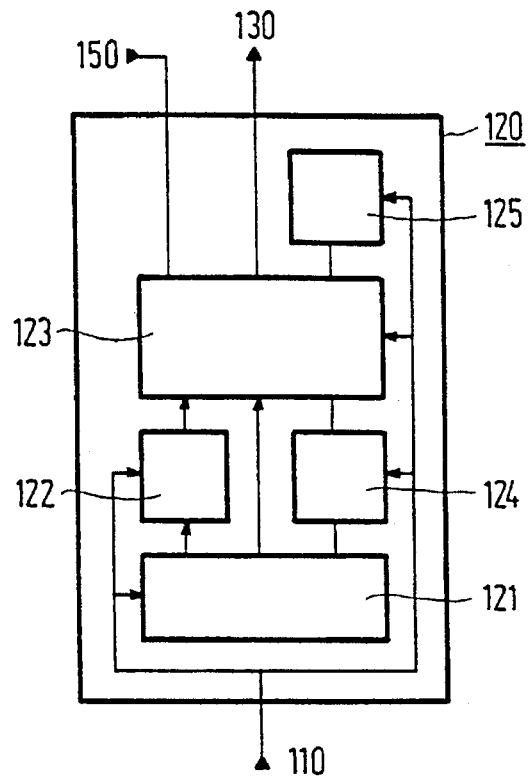
FIG. 2 shows an example of a control unit for an electric toothbrush in accordance with the invention.

In FIG. 2 an example of a control unit 120 for an electric toothbrush in accordance with the invention is shown. The control unit 120 comprises a time-measuring means 121 and a pressure-measuring means 122, a computing means 123, a position-determining means 124 and an infra-red transmitter 125. The aforesaid parts 121, 122, 123, 124, 125 are electrically connected to the supply unit 110 to receive a supply voltage. The computing means 123 is further electrically connected to the driving means 130 to control the electro-mechanical means 131 and to the switch 150 to receive a state indication (on/off). The computing means 123, which is the pivot of the control unit 120, is electrically connected to the time-measuring means 121 to receive the duty time, to the pressure-measuring means 122 to receive the duty pressure, to the position-determining means 124 to receive the duty position and to the infra-red transmitter 125 to control the indication means 210. In the control unit 120 as shown the time-measuring means 121 is also electrically connected to the pressure-measuring means 122 and the position-determining means 124, since the duty pressure and the duty position may be determined in dependence on the duty time.

The time-measuring means 121 and the pressure-measuring means 122 can be constructed in conventional ways as known from the prior art. However, the time-measuring means 121 and the pressure-measuring means 122 may be adapted to register the duty time and the duty pressure in response to the difference of the present current and the idle current of the electro-mechanical means 131. The present current is the current consumed by the electro-mechanical means 131 when the user exerts pressure on the brush. The idle current is the current consumed by the electro-mechanical means 131 when the toothbrush is moving freely. The present current may be monitored by a first comparator, whose first and second inputs are coupled across a resistor, which is serially coupled to the electro-mechanical means 131 to conduct its supply current, and whose output is coupled to a second comparator to detect and register the idle current as a returning dip in the characteristic of the supply current of the electro-mechanical means 131. As to that the second comparator may have a first input which is coupled to the output of the first comparator to sample the output signal, a second input which is coupled to a memory cell comprising an updated value corresponding to the idle current, and an output which is coupled to a logic circuit to detect and register a returning dip. In this way the duty time is measured only if the user exerts pressure on the brush. By monitoring the idle current and storing its actual value in a register or non-volatile memory, any change in the idle current caused by ageing or the like is tracked. During use of the electric toothbrush the user occasionally removes the brush from his teeth, for instance when he changes the position of the toothbrush. During these instants the current drops back from the present current value to the idle current value. The dip in the current indicates the onset of the idle current and may be used to update the value of the idle current stored in the memory by sampling the current.

The duty performance may be a value computed by taking the product of the measured duty time, the measured duty pressure and a scale factor. Under high duty pressure the duty time is given a higher weight than under lower pressure by changing the scale factor in response of the actual value of the duty pressure. In this way the duty time is stretched under low pressure conditions and compressed under high pressure conditions.

The position-determining means 124 may provide a two-position determination and may be constructed by a mercury switch, as known from electric irons, or by a permanent magnet which is movable in respect to a reed-relay contact. The two-position determination by the position-determining means 124 provides information about the handling position of the toothbrush. Preferably in a first position the toothbrush is capable to clean a left-side tooth-face, and in a second position the toothbrush is capable to clean a right-side tooth-face. The position-determining means 124 distinguishes the first handling position of the toothbrush from the second handling position of the toothbrush. The respective times spent for toothbrushing in both handling positions or the difference between the respective times can be used as a further parameter for increasing the accuracy of the computed duty performance. The measuring of the respective times may again be made dependent on the actual duty pressure by stretching the time under low pressure and compressing the time under high pressure.

As the present embodiment comprises the time-measuring means, the pressure-measuring means and the position-measuring means, the accurate determination of the duty performance is achieved by computing generally a value or number which is a mathematical operation on the duty time, the duty pressure and the duty position, which operation may be for example, the product of a scale factor, the duty time and the duty pressure, the scale factor being dependent inter alia on the duty position.

The wireless infra-red communication link between the executive device 100 and the charging device 200 enables a permanent watching of the indication means 210 by the user during toothbrushing. As the user can observe permanently the information displayed on the indication means 210, there is no need to interrupt the toothbrushing to look at the display in order to see if the user has reached a satisfactory performance. The user may further be warned by an audible signal that he has reached a predetermined performance. This is particularly advantageous in case of a non-detachable one part electrical toothbrush where the indication means 210 is mounted on the executive device 100 itself. Additionally, the electro-mechanical means 131 may be switched off automatically by the computing means 123 when the predetermined performance is reached. Circuitry for wireless communication, in particular infra-red transmission is known and may be constructed in conventional way.

Figure 3:
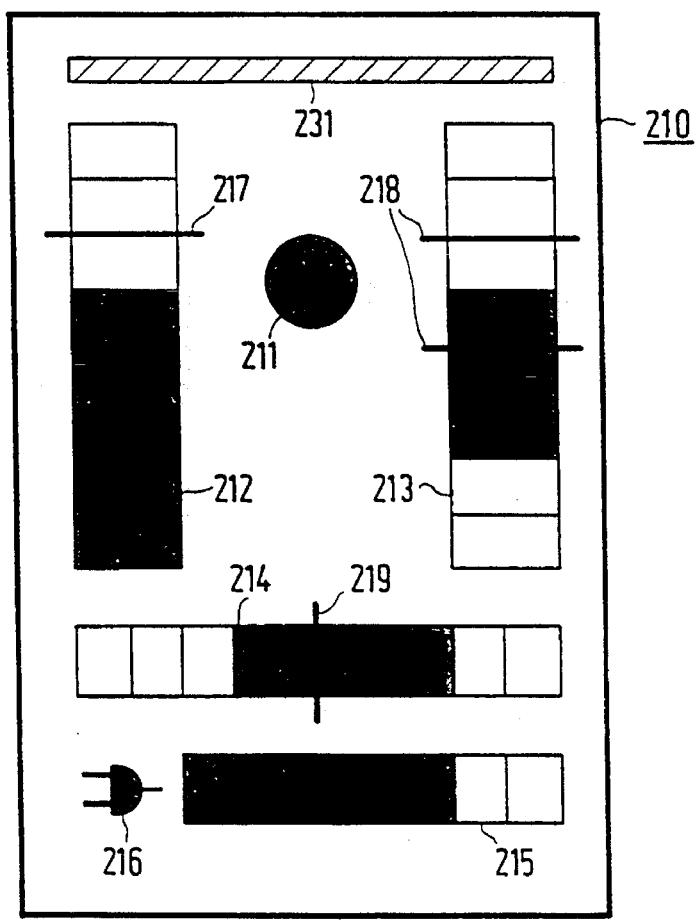
FIG. 3 shows an example of an indication means for an electric toothbrush in accordance with the invention.

In FIG. 3 an example of an indication means 210 for an electric toothbrush in accordance with the invention is shown. The indication means 210 comprises a duty performance display 211 to indicate the duty performance, a duty time display 212 to indicate the duty time, a duty pressure display 213 to indicate the duty pressure, a duty position display 214 to indicate the duty position and a supply status display 215,216 to give information about the energy status of the supply unit 110. Additionally, the indication means 210 comprises a receiving window 231 to pass the infra-red transmission light to the infra-red receiver 230. The duty performance display 211 is constructed as a lamp, which blinks when the computed performance exceeds a threshold. The duty performance display 211 may further be constructed as a segmental histogram as shown for the duty time display 212. The duty time display 212 is constructed as a segmental histogram, in which histogram a single threshold 217 indicates the minimum time to achieve a satisfactory performance. The duty pressure display 213 is also constructed as a segmental diagram, in which diagram a dual threshold 218 indicates the minimum and maximum pressure to achieve a satisfactory performance and in which diagram the exercised pressure is displayed as a segmental interval. The duty position display 214 is constructed as a segmental diagram, in which a single threshold 219 indicates the ideal result of the left/right partitioning. In the duty position display 214 the respective times are scaled and indicated in the left part and the right part of the display. The supply status display 215, 216 is constructed as a segmental histogram 215 and a lamp display 216. The subject histogram 215 and display 216, as well as the associated driving circuitry, are known per se from a plurality of marketed shavers. In the supply status display 215,216 the histogram 215 gives an indication of the amount of charge in the rechargeable battery and the lamp 216 blinks when the amount of charge reaches a minimum level.

Figure 4:
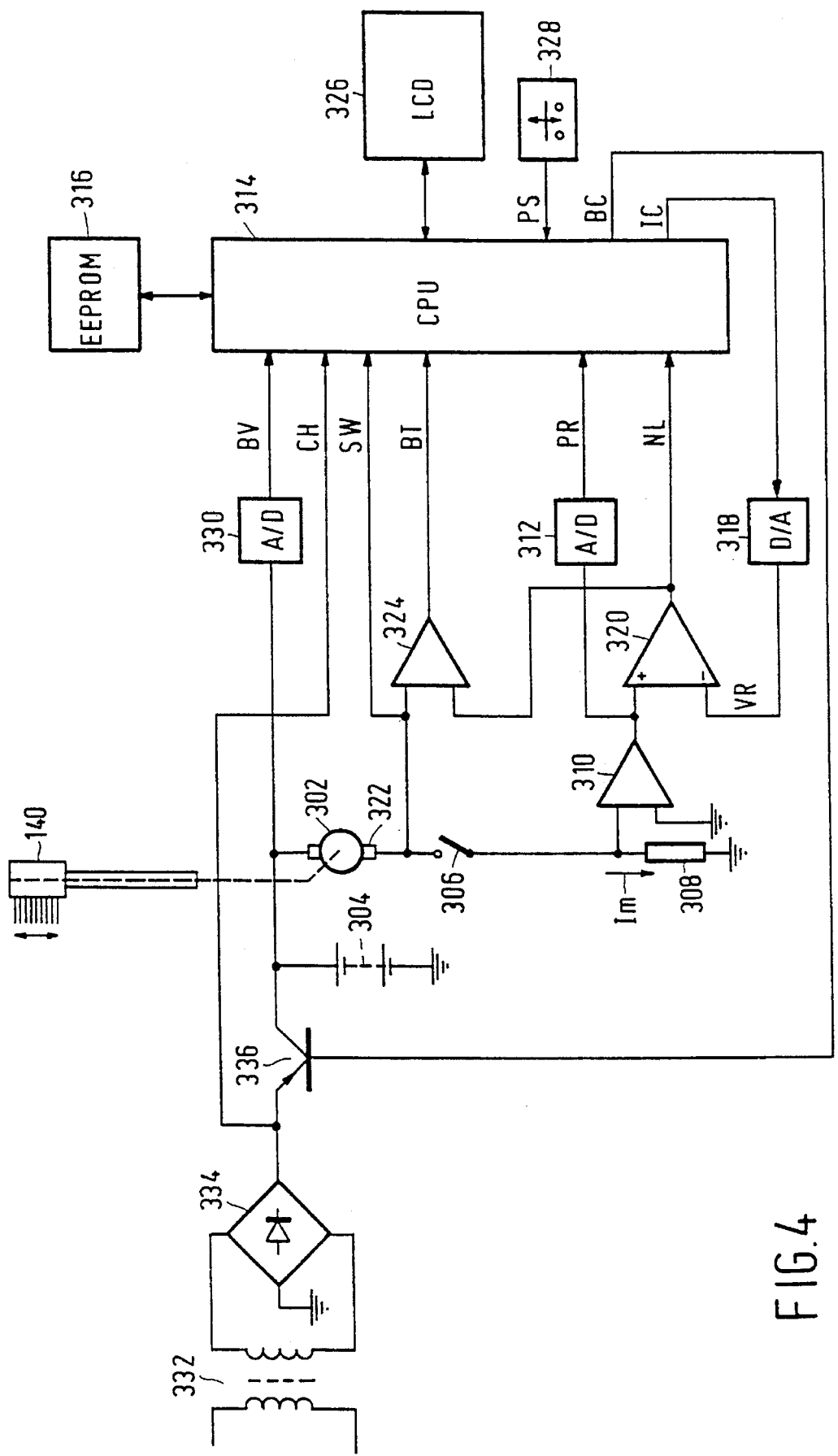
FIG. 4 shows a circuit diagram of an embodiment of an electric toothbrush in accordance with the invention.

FIG. 4 shows a circuit diagram of an embodiment of the electric toothbrush according to the invention. The brush 140 is driven by a motor 302 which receives supply voltage from the positive pole of a rechargeable battery 304 when a switch 306 is closed. The motor current Im flows via a series resistor 308 to the negative pole of the rechargeable battery 304, which negative pole also serves as ground. The motor current Im develops a voltage drop across the series resistor 308, which is amplified by an amplifier 310. The analog output voltage of amplifier 310 is convened to a digital signal PR in a first analog-to-digital converter (ADC) 312. The digital signal PR is proportional to the present value of the motor current Ira. When pressure is exerted on brush 140, more current is drawn by the motor 302 to keep the brush 140 in motion. Therefore the present value of the motor current Im, and thus also the digital signal PR is a measure of the pressure exerted on the brush during brushing. The digital signal PR is fed to a central processing unit (CPU) 314 which is programmed to store the digital signal PR in a non-volatile memory 316, for instance an EEPROM, when no pressure is exerted on the brush 140. The motor current Im is than equal to the idle current under no load conditions. The CPU 314 outputs a digital signal IC which represents the value of the idle current to a digital-to-analog converter (DAC) 318. DAC 318 converts digital signal IC to an analog reference voltage VR, which is compared with the analog output voltage of the amplifier 310 in a first comparator 320. The output signal NL of the first comparator 320 is fed to the CPU 314 and indicates whether or not the present motor current Im is greater than the idle current. Signal NL thus indicates a no load condition and signals the CPU 314 that the digital number representing the idle current stored in memory 316 may be updated. In the CPU 314 the idle current value is subtracted from the present current value and the resulting value is used for further computations. When switch 306 is closed, motor 302 is connected to ground via the series resistor 308 and a negative voltage jump occurs at the ground side terminal 322 of motor 302. This jump is used as a switching signal SW which is fed to the CPU 314 to indicate the on-switching of motor 302. The output signal NL of the first comparator 320 and the switching signal SW are connected to inputs of a second comparator 324. The second comparator 324 generates a brushing time signal BT which is also fed to the CPU 314. The brushing time signal BT thus indicates that motor 302 is running and is being loaded by pressure exerted by the user of the toothbrush. The CPU 314 is programmed to count the brushing time indicated by signal BT, to subtract the idle current stored in memory 316 from the actual current indicated by signal PR and to output the brushing time and the brushing pressure to a display 326, for example a liquid crystal display (LCD). The CPU 314 is further programmed to compute the duty performance in response of the brushing time and the brushing pressure according to an algorithm. For example, the brushing time is weighted in dependence on the actual pressure. A high pressure causes a quicker counting of timing pulses and a lower pressure causes a slower counting of timing pulses. The duty performance is the sum of the accumulated timing pulses, which sum is also output to the display 326. A satisfactory duty performance is reached when the sum of the accumulated timing pulses passes a predetermined number.

A position signal PS generated by a position switch 328, for instance a reed-relay and a movable magnet, may be further connected to the CPU 314 in order to provide information about the handling position of the toothbrush. The CPU 314 is programmed to increment a counter during a first value of the position signal PS and to decrement the counter during a second value of the position signal PS. Ideally the number of increments should be equal to the number of decrements. The difference between the two numbers is output to the display 326 and informs the user about the symmetry of his brush handling. A special warning signal may be generated and output to the display to inform the user that the symmetry is not sufficient. The position detection, the calculation of the difference and the display of the difference can be used entirely separately from the aforementioned duty performance calculation and indication and may been seen as an alternative way to determine a duty performance of an electrical toothbrush. However, the position information may be incorporated advantageously in the algorithm of the aforementioned duty performance calculation. For instance, the accumulation of the timing pulses can be made dependent on the number of increments and decrements, so that the required duty performance is reached only when the user operates the toothbrush equally in both positions. Since the display informs the user not only about the duty performance, but also about the actual values of the individual parameters (time, pressure and, optionally, position), the user is able to perceive why the duty performance aimed at is not reached at all, because he is informed that for instance, the pressure is too low. The thresholds 217, 218 and 219 shown in FIG. 3 can be useful to inform the user about his shortcomings. The display may further be provided with symbols for prompting the user to exert more pressure and/or to spend more time and/or to change his handling symmetry.

The voltage of the rechargeable battery is monitored by a second ADC 330 and applied to the CPU 314 as a digital battery voltage signal BV. The battery voltage signal BV, the switching signal SW and the pressure signal PR are used to compute the state of charge of the battery 304, to store a corresponding value in the non-volatile memory 316 and to display this value as shown in FIG. 3. The battery 304 is recharged using a transformer 332, a rectifier 334 and a switching transistor 336, which is switched on and off under control of a battery charge signal BC from the CPU 314. The rectified mains voltage CH is fed to the CPU 314 to sense whether or not mains voltage is present and to engage a suitable indication on display 326, for instance symbol 216 shown in FIG. 3, to warn the user that recharge is needed, but not possible.

The invention is not restricted to the shown embodiments and examples. Within the scope of the invention a man skilled in the art may devise further embodiments and examples. For instance, the control unit may be an intelligent unit which is based on fuzzy logic and the position-determining means may be adapted to realize a multi position determination in order to provide more information about the handling positions of the toothbrush. The handling time in each position may be used as an additional parameter to influence the calculation of the duty performance.

We claim:

1. An electric toothbrush comprising a control unit (120) comprising a time-measuring means (121) for measuring a duty time which comprises the time period of operation of the toothbrush during toothbrushing and a pressure-measuring means (122) for measuring a duty pressure which comprises the pressure exerted during operation of the toothbrush during toothbrushing, a driving means (130), which is electrically coupled to the control unit (120), the driving means (130) comprising an electro-mechanical means (131) for driving a brush (140), and an indication means (210), which is driven by the control unit (120) for informing a user of the electric toothbrush, wherein the control unit (120) further comprises a computing means (123) for computing a duty performance from the duty time and the duty pressure, the time-measuring means (121) and the pressure-measuring means (122) driving the computing means (123) and the computing means (123) driving the indication means (210), and wherein the indication means (210) is operative to inform the user of performance during or after toothbrushing.

2. An electric toothbrush as claimed in claim 1, wherein the performance is a duty performance which is the product of a scale factor, the duty time and the duty pressure.

3. An electric toothbrush as claimed in claim 2, wherein the control unit (120) is adapted to monitor a current, which is carried by the electro-mechanical means (131), the time-measuring means (123) being operative to register the duty time in response to the difference of the present current and the idle current.

4. An electric toothbrush as claimed in claim 2, wherein the control unit (120) is adapted to monitor a current, which is carried by the electro-mechanical means (131), the pressure-measuring means (122) being operative to register the duty pressure in response to the difference of the present current and the idle current.

5. An electric toothbrush as claimed in claim 2, wherein the indication means (210) comprise a display (211) for indicating the performance.

6. An electric toothbrush as claimed in claim 2, wherein the indication means (210) comprise a display (212) for indicating the duty time.

7. An electric toothbrush as claimed in claim 2, wherein the indication means (210) comprise a display (213) for indicating the duty pressure.

8. An electric toothbrush as claimed in claim 1, wherein the control unit (120) further comprises a position-determining means (124) to determine a duty position which is the position of the toothbrush during toothbrushing, the position-determining means (124) driving the computing means (123) and the computing means (123) driving the indication means (210), and wherein the computing means (123) is operative to compute the performance from the duty position.

9. An electric toothbrush as claimed in claim 8, wherein the performance is a duty performance which is an operation of the duty time, the duty pressure and the duty position.

10. An electric toothbrush as claimed in claim 9, wherein the control unit (120) is adapted to monitor a current, which is carried by the electro-mechanical means (131), the time-measuring means (123) being operative to register the duty time in response to the difference of the present current and the idle current.

11. An electric toothbrush as claimed in claim 9, wherein the control unit (120) is adapted to monitor a current, which is carried by the electro-mechanical means (131), the pressure-measuring means (122) being operative to register the duty pressure in response to the difference of the present current and the idle current.

12. An electric toothbrush as claimed in claim 9, wherein the indication means (210) comprise a display (211) for indicating the performance.

13. An electric toothbrush as claimed in claim 9, wherein the indication means (210) comprise a display (212) for indicating the duty time.

14. An electric toothbrush as claimed in claim 9, wherein the indication means (210) comprise a display (213) for indicating the duty pressure.

15. An electric toothbrush as claimed in claim 8, wherein the control unit (120) is adapted to monitor a current, which is carried by the electro-mechanical means (131), the time-measuring means (123) being operative to register the duty time in response to the difference of the present current and the idle current.

16. An electric toothbrush as claimed in claim 8, wherein the control unit (120) is adapted to monitor a current, which is carried by the electro-mechanical means (131), the pressure-measuring means (122) being operative to register the duty pressure in response to the difference of the present current and the idle current.

17. An electric toothbrush as claimed in claim 1, the control unit (120) is adaptable to monitor a current, which is carried by the electro-mechanical means (131), the time-measuring means (123) being operative to register the duty time in response to the difference of the present current and the idle current.

18. An electric toothbrush as claimed in claim 7, wherein the control unit (120) is operative to measure and register the idle current, a returning dip in the characteristic of the current being recognised as the idle current.

19. An electric toothbrush as claimed in claim 17, wherein the control unit (120) is adapted to monitor a current, which is carried by the electro-mechanical means (131), the pressure-measuring means (122) being operative to register the duty pressure in response to the difference of the present current and the idle current.

20. An electric toothbrush as claimed in claim 1, wherein the control unit (120) is adaptable to monitor a current, which is carried by the electro-mechanical means (131), the pressure-measuring means (122) being operative to register the duty pressure in response to the difference of the present current and the idle current.

21. An electric toothbrush as claimed in claim 20, wherein the control unit (120) is operative to measure and register the idle current, a returning dip in the characteristic of the current being recognized as the idle current.

22. An electric toothbrush as claimed in claim 1, wherein the indication means (210) comprise a display (211) for indicating the performance.

23. An electric toothbrush as claimed in claim 1, wherein the indication means (210) comprise a display (212) for indicating the duty time.

24. An electric toothbrush as claimed in claim 1, wherein the indication means (210) comprise a display (213) for indicating the duty pressure.

25. An electric toothbrush as claimed in claim 21, wherein the duty pressure is displayed as a segmental interval.

26. An electric toothbrush as claimed in claim 1, wherein the indication means (210) comprise a display (214) for indicating the duty position.

27. An electric toothbrush as claimed in claim 1, wherein the indication means (210) have a continuous display during toothbrushing.

28. An electric toothbrush as claimed in claim 1, wherein the indication means (210) have a temporary display after or before toothbrushing.

29. An electric toothbrush as claimed in claim 1, wherein the electric toothbrush further comprises a charge device (200), the charge device (200) comprising a charge unit (220) to charge a rechargeable battery (304) in a supply unit (110), the supply unit (110) being coupled electrically to the control unit (120).

30. An electric toothbrush as claimed in claim 29, wherein the indication means (210) is located in the charge device (200), the control unit (120) and the charge device (200) being coupled by means of a wireless communication link.

31. An electric toothbrush as claimed in claim 30, wherein the wireless communication link comprises an infra-red transmitter (125) located at the control unit (120) and an infra-red receiver (230) located at the charge device (200), the wireless communication being achieved by an infra-red transmission.

32. An electric toothbrush as claimed in claim 29, wherein the indication means (210) comprise a display (215,216) for indicating a status of the supply unit (110).

* * * * *